United States Patent [19]

Mina

[11] 4,340,767

[45] Jul. 20, 1982

[54] ANTIOXIDANT PROCESS USING FORMALDEHYDE

[75] Inventor: George L. Mina, Orangeburg, S.C.

[73] Assignee: Ethyl Corporation, Richmond, Va.

[21] Appl. No.: 263,768

[22] Filed: May 14, 1981

[51] Int. Cl.³ .............................................. C07C 39/12
[52] U.S. Cl. ..................................... 568/720; 568/718
[58] Field of Search ................................ 568/720, 718

[56] References Cited

U.S. PATENT DOCUMENTS

| | | | |
|---|---|---|---|
| 2,905,737 | 9/1959 | Webb | 568/720 |
| 2,929,849 | 3/1960 | Webb | 568/720 |
| 3,026,264 | 3/1962 | Rocklin et al. | |
| 3,309,339 | 3/1967 | Barton et al. | 568/720 |
| 3,644,538 | 2/1972 | Starnes | 568/720 |
| 3,689,572 | 9/1972 | Ruppert et al. | 568/720 |
| 3,925,488 | 12/1975 | Shin | 568/720 |
| 4,259,534 | 3/1981 | Gurvich et al. | 568/720 |

FOREIGN PATENT DOCUMENTS 1910793 9/1970 Fed. Rep. of Germany ...... 568/720

*Primary Examiner*—Werren B. Lone
*Attorney, Agent, or Firm*—Donald L. Johnson; Joseph D. Odenweller; John F. Hunt

[57] ABSTRACT

Small amounts of paraformaldehyde and a carboxylic acid are added to a reaction mixture of trialkylbenzene and 3,5-dialkyl-4-hydroxybenzyl alcohol to thereby increase the yield of the product: trialkyl-tris(3,5-dialkyl-4-hydroxybenzyl)benzene. The reaction catalyst, sulfuric acid or a Friedel-Crafts catalyst, is not adversely affected by the additional ingredients.

16 Claims, No Drawings

ANTIOXIDANT PROCESS USING FORMALDEHYDE

BACKGROUND OF THE INVENTION

I. Field of the Invention

This invention relates generally to processes for forming antioxidants and similar compounds. This invention relates more particularly to improvements in a process for the formation of a trialkyl-tris(3,5-dialkyl-4-hydroxybenzyl)benzene with a sulfuric acid catalyst or a Friedel-Crafts catalyst.

II. Description of the Prior Art

The products formed by the process of the present invention and earlier similar processes have been widely used as antioxidants in food, animal feed, stock chemicals and the like. Such antioxidant use has also proven especially valuable and effective in polymeric materials and rubbers.

The process presently used for production of the above-mentioned antioxidant products comprises two main steps. Such a process is set forth in Rocklin et al, U.S. Pat. No. 3,026,264, which patent is incorporated herein by reference.

A 3,5-dialkyl-4-hydroxybenzyl alcohol precursor is formed by the potassium hydroxide/isopropyl alcohol condensation of dialkylphenol and formaldehyde. After neutralization of the reaction mass with, e.g., acetic acid and isolation of the reaction mass, the product of the first step is reacted with a trialkylbenzene in the presence of a catalyst. The yields from the known process are inconsistent but within the range of about 55–75%.

Various techniques to improve yields have been tried but have proven to be inconsistent at best. Equipment modifications and reaction mass agitation have not resulted in consistently good yields. Thus, any improvement which would reliably yield increased amounts of product and decreased amounts of by-products would be extremely valuable. The demand for the antioxidant products is high, in some cases so great as to justify additional capital expenditure for new plant facilities.

An alternative process has been proposed for the production of the types of antioxidants discussed above. However, that alternative process has also proven to be impractical. Shin, in U.S. Pat. No. 3,925,488, has suggested carrying out the process in a low boiling inert solvent with a sulfonic acid catalyst. Shin suggests that such a process avoids undesirable dealkylation by using a low boiling solvent and minimizes the quantity of catalyst required.

Shin also suggests the gradual addition of formaldehyde to the reaction system of such a process so as to increase the yield. However, the yield increase was not very high. The overall performance and cost-effectiveness of the Shin process have proven to be poor.

SUMMARY OF THE INVENTION

The present invention is an improved process for the production of trialkyl-tris(3,5-dialkyl-4-hydroxybenzyl)benzene including the coaddition of formaldehyde and a carboxylic acid.

In a process for the production of trialkyl-tris(3,5-dialkyl-4-hydroxybenzyl)benzene, said process comprising reacting, in the liquid phase, trialkylbenzene with 3,5-dialkyl-4-hydroxybenzyl alcohol in the presence of a catalyst selected from the group consisting of sulfuric acid and Friedel-Crafts catalysts the present invention comprises the addition of formaldehyde and a carboxylic acid to the reaction mixture to thereby improve the yield of trialkyl-tris(3,5-dialkyl-4-hydroxybenzyl)benzene, wherein the alkyl groups of said alcohol are $C_1$–$C_8$ and the alkyl groups of said trialkylbenzene are $C_1$–$C_4$.

It is, therefore, an object of the present invention to provide a process which will increase the yield of the products in the above-described basic process.

It is also an object of the present invention to provide an improved process which lowers the quantity of unwanted by-products.

Furthermore, it is an object of the present invention to provide a process where small portions of relatively inexpensive commodities may be added to the above-described known process so as to improve the yield of desired products.

Finally, it is also an object of this invention to provide a process improvement by addition of paraformaldehyde and a carboxylic acid.

These and other objects, advantages, and applications of the present invention will become apparent to those skilled in the art by a reading of the following description of examples of the best mode contemplated for practicing the invention.

DESCRIPTION OF THE PREFERRED EMBODIMENT

A preferred embodiment of the invention is an improvement in the process of making 1,3,5-trimethyl-2,4,6-tris(3,5-dialkyl-4-hydroxybenzyl)benzene comprising reacting 3,5-dialkyl-4-hydroxybenzyl alcohol with mesitylene in the presence of a catalytic portion of either sulfuric acid or a Friedel-Crafts catalyst.

Alcohols suitable for use in this improved process are compounds such as are described in Rocklin et al. More generally, the alcohols have alkyl groups containing from four to about 20 carbon atoms. The following alcohols are exemplary:

3,5-di-tert-hexyl-4-hydroxybenzyl alcohol
3-methyl-5-tert-butyl-4-hydroxybenzyl alcohol
3,5-di-tert-dodecyl-4-hydroxylbenzyl alcohol
3,5-di-tert-butyl-4-hydroxybenzyl alcohol
3,5-di-tert-octyl-4-hydroxybenzyl alcohol
3,5-di-tert-eicosyl-4-hydroxybenzyl alcohol
and the like.

Tertiary alkyl groups are preferred and 3,5-di-tert-butyl-4-hydroxybenzyl alcohol is most preferred. The reaction ratio of 3,5-di-tert-alkyl-4-hydroxybenzyl alcohol to mesitylene is preferably about 3.5:1. Since the alcohol is often formed from a process resulting in about 5–15% impurities including the di-tertiary alkylphenol from which the alcohol is formed, allowance must be made to provide the desired ratio of about 3.5:1.

Until the results of this invention were proven, the probable formation of undesirable by-products militated against augmenting the reaction mass to increase the yield. It was thought that the addition of a small portion of formaldehyde would decrease the yield of desired product. Laboratory testing conducted to determine the effect on overall yield of acetic acid (a carboxylic acid) addition to the reaction mixture for the production of 1,3,5-trimethyl-2,4,6-tris(3,5-di-tert-butyl-4-hydroxybenzyl)benzene is inconclusive, but the testing indicated some yield increase. Nevertheless, it has not been possible to reproduce the increase on a large scale.

Tests conducted to determine the effect on overall yield of paraformaldehyde addition showed no increase in yield.

Quite surprisingly, the coaddition of small amounts of formaldehyde, e.g., paraformaldehyde, and a carboxylic acid such as acetic acid, provides a synergistic effect and gives significantly improved yields for reactions of the type described above. The improved yield may be achieved both in the laboratory and on a larger scale.

The following example serves to illustrate the improved process of the present invention.

EXAMPLE

Reactor

From a graduated cylinder, 138 cc methylene chloride is charged to a 1 liter Morton, creased, three-neck, round botton flask. The flask is equipped with a mechanical stirrer having a 3″ half-moon impeller, a thermometer and a side arm dropping funnel. About 10.17 gms (0.0846 mole) of mesitylene is charged from a weighed syringe. A stoichiometric excess (about 3.3 moles ratio on mesitylene) of 3,5-di-tert-butyl-4-hydroxybenzyl alcohol is calculated and charged to the flask. An adjustment must be made for the purity of the alcohol so that the appropriate mole ratio is maintained. The alcohol often contains as much as 13% impurities such as potassium salts remaining from synthesis. About 3% 2,6-di-tert-butylphenol is frequently present in the alcohol. It is not economically advantageous to purify the alcohol prior to reaction since the process of this invention tolerates the impurities quite well. Of course, the alcohol may be purified as desired. An analysis of the alcohol feed must be made to determine the impurity. In this instance, 70.01 gms of 99+% pure alcohol (0.296 mole) provide the stoichiometric ratio of 3.5:1. About 3.0 cc of acetic acid is then added.

The flask is cooled to 5° C. with an ice bath (no salt) and agitation is controlled at 125 rpm by setting a Heller GT-21 controller to about 2.5. About 0.42 gm of flake paraformaldehyde is charged to the flask while maintaining a slow nitrogen flush. Thereafter, 48 cc of 84% sulfuric acid catalyst is added dropwise over 4–5 hours while maintaining the temperature at about 3°–7° C. After all of the sulfuric acid has been added, the reaction mix is stirred an additional 15 minutes. The entire reaction mass is poured into a separatory funnel and allowed to settle for about 15 minutes. The lower (acid) phase is then cut off and discarded. The upper (product) layer is charged to the wash kettle.

Wash Kettle

The wash is carried out in a 1 liter steam jacketed, four-neck flask having a bottom stop cock. A mechanical agitator, thermometer, and nitrogen flush are provided.

About 242 cc of deionized water, 7 gms of sodium carbonate, and the reaction mass are charged to the wash flask in that order. Steam is applied to the jacket. The agitator and nitrogen flush continue during the distillation and reflux. Thereafter, the methylene chloride solvent is stripped off to depletion at 85° C. and 150 rpm. Reflux glassware is attached to the flask and about 550 cc of heptane solvent is added. The combination is heated to reflux, thereby dissolving all solids. The solution is then allowed to settle whereupon the lower, aqueous phase is cut off and discarded. The upper phase, which contains the product dissolved in heptane is washed twice with 200 cc portions of deionized water. The wash is repeated if the pH is not about 5–7 after the second wash. The temperature is maintained at about 85° C. throughout the wash by means of the steam jacket.

Crystallizer

The wash kettle solution is transferred through a 10 micron fritted glass disk to a 1 liter, three-neck, round bottom flask while maintaining a nitrogen flush. The flask is equipped with a mechanical stirrer and a thermometer. The solution is allowed to cool down to 40° C. in air with slow agitation. Thereafter, the solution is chilled to 3°–5° C. with an ice bath and held at that temperature for about 30 minutes. The product is filtered on a Buchner filter and washed with about 88 cc of room temperature heptane. The product is dried to constant weight in a vacuum oven at about 50° C. yielding 56.99 gms of substantially pure trimethyl tris(3,5-di-tert-butyl-4-hydroxybenzyl)benzene—86.89% of theoretical yield based on mesitylene charged.

The above especially preferred embodiment represents a significant improvement over previous average yields of about 65–75% product.

Permutations and variations of the above-described process yield similar good results of about 83–86% yield so long as at least about 0.5% paraformaldehyde on weight of alcohol is used in coaddition with about 4% carboxylic acid on weight of alcohol. Of course, formaldehyde may be used rather than paraformaldehyde, but the water solvent normally associated with formaldehyde may interfere somewhat with the process to lower the overall yield slightly. Other forms of formaldehyde such as trioxane may also be used successfully.

The improved results are obtainable on a large scale or at the laboratory level. Additional tests were run using 4.0 weight percent acetic acid and about a 3.5:1 mole ratio of alcohol to mesitylene and, according to the variables given below, resulted in the yields shown.

| Paraformaldehyde Weight Percent on Alcohol | Percent Yield |
| --- | --- |
| 0 | 65.22 |
| 0 | 73.95 |
| 5.2 | 82.75 |
| 3.6 | 85.62 |
| 2.2 | 86.11 |
| 1.6 | 84.54 |
| 0.89 | 84.12 |
| 0.63 | 84.16 |
| 0.60 | 84.69 |
| 0.29 | 81.95 |

The first two lines in the above table are exemplary of the basic process upon which the present invention improves. The last line of the above table demonstrates the diminishing yield at such low proportions of paraformaldehyde. Although 0.1–6.0 weight percent paraformaldehyde will effect an improved yield, about 0.4–4.0 weight percent is preferred with about 2.5 weight percent being especially preferred.

About 0.5–12 weight percent carboxylic acid on weight of alcohol is effective to bring about the benefits of the invention so long as a sufficient amount of a paraformaldehyde compound is also added. A preferred weight percent range for the carboxylic acid is 2.0–5.0% with 3.7–4.0% being especially preferred for most carboxylic acids.

The carboxylic acids suitable for this invention include those of the formula RCOOH wherein R is H (formic acid) or $C_1$–$C_{10}$ alkyl. Formic acid and the $C_1$–$C_4$ carboxylic acids are preferred and acetic acid is especially preferred due to its availability and strong synergistic effect with formaldehyde, especially paraformaldehyde, in the inventive process.

Available solvents for the reaction of this invention include paraffins, especially $C_5$–$C_{10}$ compounds such as pentane, isopentane, hexane, cyclohexane, heptane, octane, isooctane and decane as well as mixtures of these, or the mixture of hydrocarbons known as "petroleum ether." More suitable are halogenated solvents such as the alkylene halides including 1,1-dichloropropane, 1,2-dichloropropane, 2,2-dichloropropane, 1,1-dichloroethane, 1,2-dichloroethane, 1,1,1-trichloroethane, n-butylchloride, sec-butyl chloride, isobutyl chloride, chloroform, carbon tetrachloride, and the like with methylene chloride being an especially preferred solvent.

The amount of solvent may vary so long as dissolution of the ingredients is achieved where necessary. Generally, less of the chloroalkane solvents is required. A useful range is about 50–500 parts of solvent per 100 parts of reactant. A preferred range is from 100–200 parts of solvent per 100 parts of reactant.

Although not desiring to be bound by any particular theory of reaction mechanism, it is believed that the improved process may proceed by initial formation of the quinone methide intermediate:

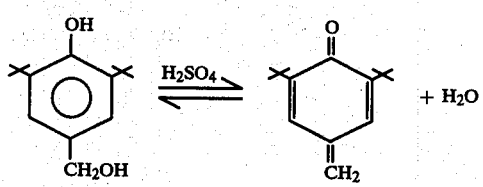

Thereafter the quinone may react with the mesitylene to stepwise form first a two-ring structure, then a three-ring structure, and finally the desired fully substituted benzene ring:

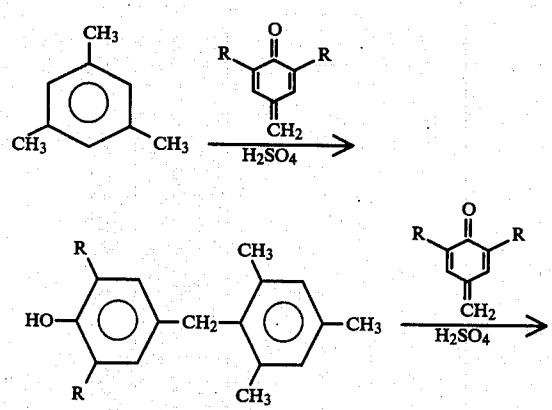

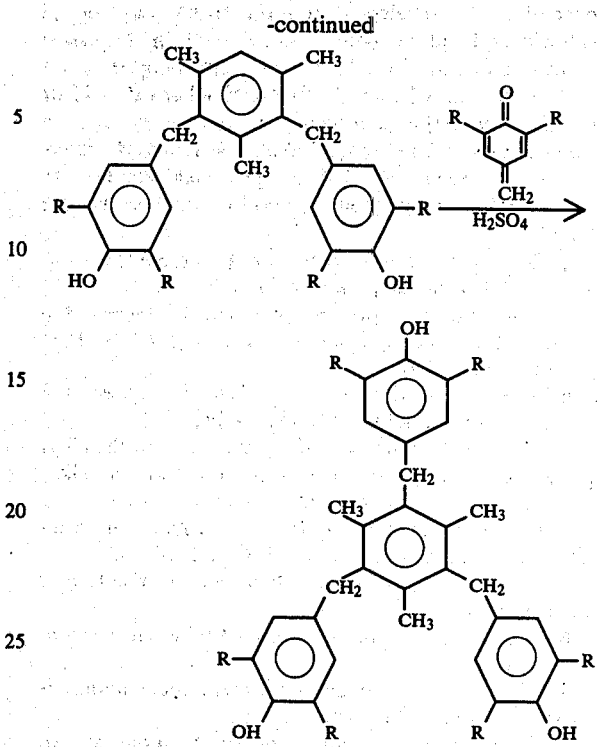

wherein all R's are the tert-butyl radical.

It may be that the carboxylic acids used in the inventive process serve to depolymerize paraformaldehyde plus perform other functions.

Although again not wishing to be bound by a particular theory, it is thought that the addition of paraformaldehyde supresses the following exemplary type of equilibrium reaction:

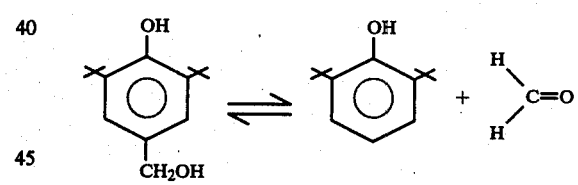

Of course, excess formaldehyde would tend to drive this equilibrum to the left. While providing an unexpected yield increase, there is no evidence that the characteristics of the product of the invention are adversely affected.

The compounds made by the process of this invention have proven antioxidant activity and are, therefore, very useful.

While preferred embodiments of the present invention have been given, the invention is not limited thereto. It is possible, for example, to vary the feed/charging techniques for the reactants, the mole ratio of alcohol to trialkylbenzene, or the amount/type of paraformaldehyde or amount of acetic acid without departing from the scope or spirit of the invention as defined by the appended claims.

I claim:

1. In a process for the production of trialkyl-tris(3,5-dialkyl-4-hydroxybenzyl)benzene, said process comprising reacting, in the liquid phase, trialkylbenzene with 3,5-dialkyl-4-hydroxybenzyl alcohol in the presence of a catalyst selected from the group consisting of sulfuric acid and Friedel-Crafts catalysts, the improvement comprising the addition of formaldehyde and a carboxylic acid of formula RCOOH where R is H or $C_1-C_{10}$ alkyl to the reaction mixture to thereby improve the yield of trialkyl-tris(3,5-dialkyl-4-hydroxybenzyl)-benzene, wherein the alkyl groups of said alcohol are $C_1-C_8$ and the alkyl groups of said trialkylbenzene are $C_1-C_4$.

2. The improved process of claim 1 wherein the formaldehyde is added as paraformaldehyde.

3. The improved process of claim 1 wherein the amount of formaldehyde added is about 0.1–6.0% of the weight of said alcohol.

4. The improved process of claim 3 wherein the amount of formaldehyde is about 2–3%.

5. The improved process of claim 1 wherein the alkyl groups of said alcohol are tert-butyl and the alkyl groups of the trialkylbenzene are methyl.

6. The improved process of claim 1 wherein the reaction is carried out between −10° C. and 100° C.

7. The process of claim 4 wherein the reaction is carried out at 5° C.

8. The improved process of claim 1 wherein the catalyst is sulfuric acid.

9. The process of claim 1 wherein the reaction is carried out in a hydrocarbon solvent.

10. The process of claim 1 wherein the mole ratio of said alcohol to said trialkylbenzene is from about 3–4:1.

11. The process of claim 1 wherein said carboxylic acid is acetic acid.

12. The process of claim 11 wherein said acetic acid is present in an amount of about 4%.

13. The process of claim 1 wherein said trialkylbenzene is mesitylene.

14. In a process for the production of trimethyl-tris(3,5-di-tert-butyl-4-hydroxybenzyl)benzene, said process comprising reacting, in the liquid phase, about 3–4 moles of mesitylene per mole of 3,5-di-tert-butyl-4-hydroxybenzyl alcohol in the presence of sulfuric acid, the improvement comprising the addition to the reaction mixture of about 0.6–2.5 weight percent paraformaldehyde and 2–5 weight percent acetic acid based on the weight of 3,5-di-tert-butyl-4-hydroxybenzyl alcohol to improve the yield of trimethyl-tris(3,5-di-tert-butyl-4-hydroxybenzyl)benzene.

15. The process of claim 8 wherein the solvent is methylene chloride.

16. In a process for the production of trialkyl-tris(3,5-dialkyl-4-hydroxybenzyl)benzene, said process comprising reacting, in the liquid phase at about −10° C. to 100° C., about 3–4 moles of trialkylbenzene per mole of 3,5-dialkyl-4-hydroxybenzyl alcohol in the presence of a catalytic portion of a substance selected from sulfuric acid and Friedel-Crafts catalysts, the improvement comprising the addition to the reaction mixture of about 0.1–6.0 weight percent formaldehyde and about 0.5–12.0 weight percent acetic acid based on the weight of said alcohol to thereby improve the yield of trialkyl-tris(3,5-dialkyl-4-hydroxybenzyl)benzene, wherein the alkyl groups of said alcohol are $C_1-C_8$ and the alkyl groups of said trialkylbenzene are $C_1-C_4$.

* * * * *